United States Patent
Bevins et al.

(10) Patent No.: US 6,497,691 B1
(45) Date of Patent: Dec. 24, 2002

(54) STRUCTURALLY DURABLE, DRAPEABLE BREATHABLE BARRIER FILM COMPOSITIONS AND ARTICLES

(75) Inventors: Errette Bevins, Waynesboro, VA (US); Jorge Santisteban, San Luis Potosi (MX)

(73) Assignee: Polymer Group, Inc., North Charleston, SC (US)

( * ) Notice: Subject to any disclaimer, the term of this patent is extended or adjusted under 35 U.S.C. 154(b) by 0 days.

(21) Appl. No.: 09/939,353

(22) Filed: Aug. 24, 2001

(51) Int. Cl.[7] ................................................ A61F 13/15
(52) U.S. Cl. ................... 604/385.01; 604/317; 604/367
(58) Field of Search ................................. 604/317–402; 2/400–406, 267, 268

(56) References Cited

U.S. PATENT DOCUMENTS

| | | |
|---|---|---|
| 3,870,593 A | 3/1975 | Elton et al. |
| 4,029,101 A | 6/1977 | Chesky et al. |
| 4,041,203 A | 8/1977 | Brock et al. |
| 4,184,498 A | 1/1980 | Franco |
| 4,195,634 A | 4/1980 | DiSalvo et al. |
| 4,308,303 A | 12/1981 | Mastroianni et al. |
| 4,329,309 A | 5/1982 | Kelly |
| 4,381,326 A | 4/1983 | Kelly |
| 4,573,986 A | 3/1986 | Minetola et al. |
| 4,845,779 A | 7/1989 | Wheeler et al. |
| 4,876,746 A | 10/1989 | Howie |
| 4,886,513 A | 12/1989 | Mason, Jr. et al. |
| 5,445,874 A | 8/1995 | Shehata |
| 5,527,302 A * | 6/1996 | Endres et al. ............. 604/385.1 |
| 5,665,374 A | 9/1997 | Hill et al. |
| 5,843,056 A | 12/1998 | Good et al. |
| 5,955,187 A * | 9/1999 | McCormack et al. .... 428/315.5 |
| 6,029,274 A | 2/2000 | Welchel et al. |
| 6,096,668 A * | 8/2000 | Abuto et al. ................ 442/328 |
| 6,103,647 A | 8/2000 | Shultz et al. |
| 6,198,018 B1 | 3/2001 | Curro |

* cited by examiner

*Primary Examiner*—Jeanette Chapman
(74) *Attorney, Agent, or Firm*—Wood, Phillips, Katz, Clark & Mortimer

(57) ABSTRACT

A thermoplastic film, and the articles thereof, consisting essentially of vinyl copolymer which exhibits sufficient structural durability and enhanced drapeability suitable for application as a breathable barrier layer in disposable end-use articles such as disposable hygiene and protective medical/industrial products. A preferred form of the vinyl copolymer are those selected from the ethylenic acrylates, with ethylene methyl acrylate being most preferred. Melt additives can be compounded with the ethylene methyl acrylate prior to extrusion include colorants, softening agents, UV stabilizers, and surface energy modifiers such as anti-static, hydrophobic and hydrophilic compounds.

8 Claims, 1 Drawing Sheet

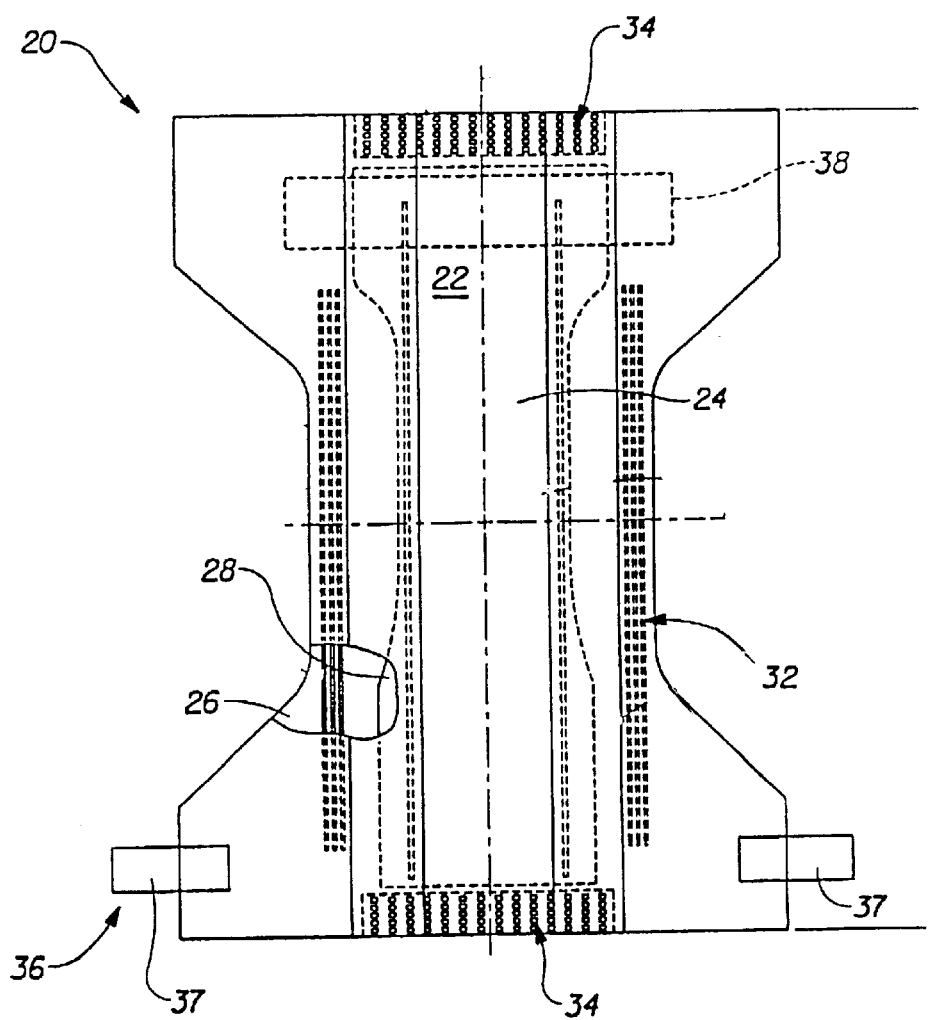

STRUCTURALLY DURABLE, DRAPEABLE BREATHABLE BARRIER FILM COMPOSITIONS AND ARTICLES

TECHNICAL FIELD

The present invention is directed to a thermoplastic film composition, and more particularly, to a thermoplastic film consisting essentially of a vinyl copolymer, which exhibits structural durability and enhanced drapeability suitable for application as a breathable barrier layer in absorbent disposable hygiene and medical/industrial protective end-use articles.

BACKGROUND OF THE INVENTION

This invention is directed to breathable barrier films, or films capable of transmitting moderate levels of water vapor but are generally resistant to the passage of water in a liquid form. Breathable films have been known and used for many years in the production of, for example, water-proof clothing, to allow for the escape of water vapor from the surface of the skin of the wearer while improving long-term comfort. Such breathable films can be broadly classified as being of a microporous or monolithic nature.

A microporous film has a large number of pores formed in the film using special processing conditions. One method of obtaining microporosity in films is described in U.S. Pat. No. 3,870,593, wherein a quantity of powdered inert material, such as calcium carbonate, is incorporated as a pore nucleating agent into a thermoplastic matrix prior to extrusion in film form. After extrusion, the loaded film is drawn, thus extending the thermoplastic matrix away from the pore-nucleating agent and inducing the formation of small pores. As described in U.S. Pat. No. 4,308,303 after production of the microporous film, the film may be subsequently coated with fibers to produce a laminate. The lamination of microporous films to fabrics is practicable by a number of well-known and acceptable methods, including adhesive and thermal bonding.

Due to the mode of pore formation in microporous films creating a pathway through the protective film, such films are not suitable for certain applications. The indiscriminate passing of dangerous gases, vapors and biological agents, such as viral pathogens, would be contraindicated in end-uses whereby protection from such dangerous material is desirable, if not critical.

A second class of breathable films is referred to as monolithic films, in which the film offers a generally uniform construction which is free of pores. Monolithic breathable films are capable of allowing the transfer of certain gases and liquid vapors due to chemical absorption into the film matrix and subsequent transfer through the film thickness and release on the opposite film facing. For films, a high rate of moisture transmission is driven by the relatively high concentration and pressure of vapor on one side of the film. This mechanism of transfer is described in U.S. Pat. No. 5,445,874, which discloses thin films of certain polyurethanes that possess inherently water vapor transmission rates higher than the human skin, allowing the film to be used as an outer layer in burn dressings.

As practiced monolithic films require a change in the thickness of the film in order to modify the water vapor transfer rate (WVTR) performance, with thinner films providing higher WVTR's. As the thickness of a monolithic film is modified in order to adjust the WVTR, and particular when such films are reduced in caliper, the risk increases that a tear or imperfection may occur which will compromise the effectiveness of the barrier properties. Also, these breathable films tend to be harsh and noisy when combined with substrate materials and do not have an attractive visual appearance or a favorable fit to the user.

An unmet need exists for a breathable barrier film, with good WVTR properties, which exhibits sufficient structural durability necessary to maintain barrier performance and improved drapeability for enhanced fit and user comfort.

SUMMARY OF THE INVENTION

In accordance with the present invention, a thermoplastic film composition, and more particularly, a monolithic thermoplastic film comprising of a vinyl copolymer which exhibits sufficient structural durability and enhanced drapeability suitable for application as a breathable barrier layer in disposable end-use articles such as disposable hygiene and protective medical/industrial products. The film exhibits a WVTR of at least about 140 and no more than about 450.

The film is composed primarily of an vinyl copolymer, which can optionally be formed into a homogeneous and uniform blend with at least one melt additive. The film exhibits enhanced drapeability and strength for structurally durable breathable barrier performance with the additional benefit of favorable adhesion to a broad number of component polymers and substrate materials when utilized in laminate constructs.

Suitable vinyl copolymers include those families of polymers as well as acetates and acrylates. A preferred form of the vinyl copolymer are those selected from the ethylenic acrylates, with ethylene methyl acrylate being most preferred. Melt additives that can be optionally compounded with the ethylene methyl acrylate prior to extrusion include colorants, softening agents, UV stabilizers, and surface energy modifiers such as anti-static, hydrophobic and hydrophilic compounds and the mixtures thereof.

Advantageously, the film of the present invention can be in cast sheet form that can be used either individually or in conjunction with other separately formed materials, or preferably, can be continuously and directly applied to a substrate material while the film is in a molten or semi-molten state. When the film is applied directly to a substrate material, such as a woven or nonwoven fabric, the film exhibits useful adhesion properties without the necessary addition of other adhesives.

It has also been found that the film of the present invention can be loaded with elevated concentrations of melt additive without undue determent to the performance of the structurally durable, drapeable barrier properties. Of particular benefit, higher concentrations of titanium dioxide can be used to significantly improve the opacity of the resultant breathable barrier film. An improvement in opacity is of particular importance in the fabrication of personal hygiene articles, whereby the increased opacity reduces the printing through of organic exudates expressed into the article during its use.

DETAILED DESCRIPTION

While the present invention is susceptible of embodiment in various forms, hereinafter is described a presently preferred embodiment of the invention, with the understanding that the present disclosure is to be considered as an exemplification of the invention, and is not intended to limit the invention to the specific embodiment illustrated.

As used herein, the term water vapor transmission rate or WVTR is a value expressed in terms of grams of transmitted moisture per square meter of film over a 24 hour or one day period as determined by the protocol and teachings of U.S. Pat. No. 5,843,056, hereby incorporated by reference.

The present invention contemplates the use of a vinyl copolymer thermoplastic resin, which can optionally be admixed with one or more melt additives and extruded or cast into thin films either as an individual film, or as a film layer applied directly upon a substrate material.

In the preferred embodiment, the vinyl copolymer thermoplastic resin is incorporated into a film in the amount of at least 80% by weight, with the remainder of the film weight comprising one or more aesthetic or performance modifying melt additives. Within the blend parameters set forth above, practical consideration must be made as to the film formation including the structural durability of the film when used alone or as a layer with a fabric, and the minimum thickness at which a film can be formed using conventional equipment. The minimum thickness is on the order of 0.1 to 0.2 thousandths of an inch, and the maximum thickness can extend up to about 2 thousandths of an inch. A thin film having a higher amount of colorant might be used, for example, as an outer barrier for a hygiene product such as diapers. Thicker films might be employed in articles where structural durability and extensive barrier performance is a more important factor, such as in medical or industrial protective products.

The formation of finite thickness films from thermoplastic polymers is a well-known practice. Thermoplastic polymer films can be formed by either dispersion of a quantity of molten polymer into a mold having the dimensions of the desired end product, known as a cast film, or by continuously forcing the molten polymer through a die, known as an extruded film. Extruded thermoplastic polymer films can either be formed such that the film is cooled then wound as a completed product, or dispensed directly onto a substrate material to form a composite material having performance of both the substrate and the film layers. Examples of suitable substrate materials include macroporous or apertured films, polymeric or metallic sheet stock and woven or nonwoven fabrics.

Extruded films utilizing the composition of the present invention can be formed in accordance with the following representative direct extrusion film process. Blending and dosing storage comprising at least two hopper loaders, one for the vinyl copolymer resin chip and one for pelletized melt additive amide in thermoplastic carrier resin, feed into two variable speed augers. The variable speed augers transfer predetermined amounts of polymer chip and additive pellet into a mixing hopper. The mixing hopper contains a mixing propeller to further the homogeneity of the mixture. Basic volumetric systems such as that described are a minimum requirement for accurately blending the fatty acid amide into the thermoplastic polymer. The polymer chip and melt additive pellet blend feeds into a multi-zone extruder. Upon mixing and extrusion from multi-zone extruder, the polymer compound is conveyed via heated polymer piping through a screen changer, wherein breaker plates having different screen meshes are employed to retain solid or semi-molten polymer chips and other macroscopic debris. The mixed polymer is then fed into a melt pump, and then to a combining block. The combining block allows for multiple film layers to be extruded, the film layers being of either the same composition or fed from different systems as described above. The combining block is connected to an extrusion die, which is positioned in an overhead orientation such that molten film extrusion is deposited at a nip between a nip roll and a cast roll.

When a substrate material is to receive a film layer by extrusion, a substrate material source is provided in roll form to a tension-controlled unwinder. The base layer is unwound, optionally treated with a surface modifying process, such as heating or corona discharge, and moves over the nip roll. The molten film extrusion from the extrusion die is deposited onto the substrate material at the nip point between the nip roll and the cast roll. The newly formed base layer and film composite is then removed from the cast roll by a stripper roll and wound onto a new roll.

A number of technologies are capable of forming a substrate materials suitable to receive, by bonding or direct extrusion, at least one layer of film in accordance with the present invention including those substrate materials which are formed as continuous filament nonwoven fabrics, staple fiber nonwoven fabrics, continuous filament or staple fiber woven textiles, and reticulated films. Such substrate materials are typically manufactured from: thermoplastics including polyesters, polyamides and polyolefins, thermoset polymers such as acrylics, natural fibers such as cotton, wood pulp, and viscose rayon, and the blends thereof. Since the film resides as a layer on at least one side of the substrate material, the basis weight of the substrate material is not critical, and depends on the end use of the product. Composite nonwoven fabrics can also be employed, such as multiple-beam spunbonds, meltblowns, and the layering thereof.

In general, continuous filament nonwoven fabric formation involves the practice of the spunbond process. A spunbond process involves supplying a molten polymer, which is then extruded under pressure through a large number of orifices in a plate known as a spinneret or die. The resulting continuous filaments are quenched and drawn by any of a number of methods, such as slot draw systems, attenuator guns, or Godet rolls. The continuous filaments are collected as a loose web upon a moving foraminous surface, such as a wire mesh conveyor belt. When more than one spinneret is used in line for the purpose of forming a multi-layered fabric, the subsequent webs is collected upon the uppermost surface of the previously formed web. The web is then at least temporarily consolidated, usually by means involving heat and pressure, such as by thermal point bonding. Using this means, the web or layers of webs are passed between two hot metal rolls, one of which has an embossed pattern to impart and achieve the desired degree of point bonding, usually on the order of 10 to 40 percent of the overall surface area being so bonded.

A related means to the spunbond process for forming a layer of a nonwoven fabric is the melt blown process. Again, a molten polymer is extruded under pressure through orifices in a spinneret or die. High velocity air impinges upon and entrains the filaments as they exit the die. The energy of this step is such that the formed filaments are greatly reduced in diameter and are fractured so that microfibers of finite length are produced. This differs from the spunbond process whereby the continuity of the filaments is preserved. The process to form either a single layer or a multiple-layer fabric is continuous, that is, the process steps are uninterrupted from extrusion of the filaments to form the first layer until the bonded web is wound into a roll. Methods for producing these types of fabrics are described in U.S. Pat. No. 4,043,203, incorporated herein by reference.

Currently, many nonwoven manufacturing lines include at least two spunbond stations and optionally one or more meltblown stations in between. This enables the continuous production of a composite fabric consisting of discrete spunbond and meltblown layers. These fabrics are commonly called SMS, referring to a spunbond-meltblown-spunbond arrangement of layers. Thermal point bonding, as previously described, is typically used to consolidate such webs.

Staple fibers used to form nonwoven fabrics begin in a bundled form as a bale of compressed fibers. In order to decompress the fibers, and render the fibers suitable for integration into a nonwoven fabric, the bale is bulk-feed into a number of fiber openers, such as a garnet, then into a card. The card further frees the fibers by the use of co-rotational and counter-rotational wire combs, then depositing the fibers into a lofty batt. The lofty batt of staple fibers can then optionally be subjected to fiber reorientation, such as by air-randomization and/or cross-lapping, depending upon the ultimate tensile properties of the resulting nonwoven fabric. The fibrous batt is integrated into a nonwoven fabric by application of suitable bonding means, include, but not limited to, use of adhesive binders, thermobonding by calender or through-air oven, and hydroentanglement.

Production of conventional textile fabrics is known to be a complex, multi-step process. The production of staple fiber yarns involves the carding of the fibers to provide feedstock for a roving machine, which twists the bundled fibers into a roving yarn. Alternately, continuous filaments are formed into bundle known as a tow, the tow then serving as a component of the roving yarn. Spinning machines blend multiple roving yarns into yarns that are suitable for the weaving of cloth. Certain of the weaving yarns are transferred to a warp beam, which, in turn, contains the machine direction yarns, which will then feed into a loom. Other of the weaving yarns supply the weft or fill yarns which are the cross direction threads in a sheet of cloth. Currently, commercial high speed looms operate at a speed of 1000–1500 picks per minute, whereby a pick is a single yarn. The weaving process produces the final fabric at manufacturing speeds of 1260 inches to 1980 inches per minute.

Reticulated films, such as those of U.S. Pat. Nos. 4,381,326 and 4,329,309, are representative of macroporous films. Such macroporous films, which are typically employed in the construction of disposable feminine hygiene products, exhibit apertures within the layer of reticulated film. Application of the breathable barrier film of the present invention across these apertures renders a film laminate that then exhibits controlled breathability with further enhanced barrier performance.

Utilizing the above discussed substrate material forming technologies, combinations of same or different substrate materials with one or more breathable barrier film layers can be practiced to yield composite materials of further improved and specifically tuned performance.

A number of end-use articles can be benefit from the inclusion or substitution of a pre-existing barrier layer with the breathable barrier film of the present invention, including, but not limited to, hygiene absorbent articles, such as diapers and catamenial products, and medical/industrial protective articles.

Disposable waste-containment garments, are generally described in U.S. Pat. Nos. 4,573,986, 5,843,056, and 6,198,018, which are incorporated herein by reference.

An absorbent article incorporating a vinyl copolymer breathable barrier film of the present invention is represented by the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, pull-on garments, and the like.

FIG. 1 is a plan view of a diaper 20 in an uncontracted state (i.e., with elastic induced contraction pulled out) with portions of the structure being cut-away to more clearly show the construction of the diaper 20. As shown in FIG. 1, the diaper 20 preferably comprises a containment assembly 22 comprising a liquid pervious topsheet 24; a liquid impervious backsheet 26 joined to the topsheet; and an absorbent core 28 positioned between the topsheet 24 and the backsheet 26. The absorbent core 28 has a pair of opposing longitudinal edges, an inner surface and an outer surface. The diaper can further comprise elastic leg features 32; elastic waist features 34; and a fastening system 36 which preferably comprises a pair of securement members 37 and a landing member 38.

Practical application of a vinyl copolymer resin, and preferably an ethylene methyl acrylate resin, as the primary constituent of a breathable monolithic film represented by backsheet 26 results in a diaper that is more flexible and therefore more conforming to deformation of the overall structure as the diaper is worn. Further, as the backsheet is subjected to frictional contact with the user's environment, the improved adhesion of the film to the substrate materials aid in ensuring that the overall diaper construct does not fail structurally while the diaper is in use. An additional benefit when using an ethylene methyl acrylate loaded with high levels of colorants, such as titanium dioxide, is an increase in opacity. An increase in opacity reduces the ability of urine or other excreta to alter the external coloration of the diaper article.

Catamenial products, such as feminine hygiene pads, are of the same general construction as the aforementioned diaper structure. Again, a topsheet and a backsheet are affixed about a central absorbent core. The overall design of the catamenial product is altered to best conform to the human shape and for absorbing human exudates. Representative prior art to such article fabrication include U.S. Pat. Nos. 4,029,101, 4,184,498, 4,195,634, and 4,886,513, which are incorporated herein by reference.

Medical and industrial protective products, such as CSR, medical gown, surgical drape and oversuits can benefit significantly from the inclusion of the structurally durable and drapeable breathable barrier film of the present invention. Of particular utility in the fabrication of such protective products is the application of the vinyl copolymer film in areas of high abrasion, such a knee, and elbow regions of garments and fixture zones of drapes and wraps, whereby the structural durability of the film improves product performance without determent to the barrier properties. Patents generally describing such protective products include U.S. Pat. Nos. 4,845,779, 4,876,746, 5,655,374, 6,029,274, and 6,103,647, which are incorporated herein by reference.

Additional details are provided in the following examples.

EXAMPLE 1

(Prior Art)

A nonwoven fabric/film laminate was manufactured by a conventional film extrusion process as describe above. An initial polypropylene spunbond-meltblown-spunbond (SMS) nonwoven fabric of conventional manufacture and supplied by Polymer Group, Inc., was formed by thermal calendering of an 6.5 grams per square meter spunbond layer, an interceding 3 gram per square meter meltblown layer, and a 6.5 grams per square meter spunbond layer. The SMS fabric was unwound at a line speed of 60 feet per minute and a 18 grams per square meter film was extruded there upon. The film consisted of an blend of 80% by weight low density polyethylene (LDPE) as supplied by Exxon Chemical under the code LD 202.48, and a 20% by weight ethylene methyl acrylate as supplied by AtoFina Chemical under the code Lotryl 20MA08.

EXAMPLE 2

A film/substrate material laminate made in accordance with EXAMPLE 1, wherein the alternative film of the present invention consisted of 100% by weight ethylene methyl acrylate.

EXAMPLE 3

A film/substrate material laminate made in accordance with EXAMPLE 1, wherein the alternate film of the present invention consisted of 20% by weight LDPE and 80% by weight ethylene methyl acrylate.

EXAMPLE 4

A film/substrate material laminate made in accordance with EXAMPLE 1, wherein the alternate film of the present invention consisted of 14% by weight titanium dioxide as available from A. Schulman Products as code PBA 8000N, 2% by weight anti-block as also available from A. Schulman Products as code Polybatch BF-70, and 84% by weight ethylene methyl acrylate.

EXAMPLE 5

A nonwoven fabric/film laminate was manufactured by a conventional film extrusion process as describe above. An initial polypropylene spunbond-meltblown-spunbond (SMS) nonwoven fabric of conventional manufacture and supplied by Polymer Group, Inc., was formed by the formation and thermal calendaring of an 8 grams per square meter spunbond layer, an interceding 1 gram per square meter meltblown layer, and a 6 grams per square meter spunbond layer. The SMS fabric was unwound at a line speed of about 200 feet per minute and a 11 grams per square meter film was extruded there upon. The film consisted of an blend of 7% by weight titanium dioxide, 93% by weight ethylene methyl acrylate as supplied by AtoFina Chemical under the code Lotryl 20MA08.

EXAMPLE 6

A film/substrate material laminate made in accordance with EXAMPLE 5, wherein the alternate film of the present invention consisted of 14% by weight titanium dioxide as available from A. Schulman Products as code PBA 8000N, 2% by weight anti-block as also available from A. Schulman Products as code Polybatch BF-70, and 84% by weight ethylene methyl acrylate.

Table 1 depicts the test and comparative data of Examples 1 through 4. Table 2 depicts the test and comparative data of Examples 5 and 6. Testing was conducted in accordance with the following accepted test procedures:

Cantilever Bend—ASTM D 5732-95

Tensiles—ASTM D 5035-95

Flexural Rigidity—wt (mg/cm$^2$)×(length of overhang (cm)/2)$^3$ Results for Flexural Rigidity are reported in (gm/cm$^2$)×bending length$^3$ instead of (mg/cm$^2$)×bending length$^3$ Opacity—Tested on Hunter Lab equipement ColorQUEST II colormeter.

Set up:
CIELab scale
Illuminant D65
MI Illuminate Fcw
Observer angle 10°
Indices APHA-20 mm
Opacity (y)=Y black backing/Y white backing×100

As can be seen from the data provided, the barrier film laminate comprising at least 80% by weight ethylene methyl acrylate exhibit favorable reduction in drape of at least 10% and flexural rigidity performance of at least 22%.

From the foregoing, it will be observed that numerous modifications and variations can be affected without departing from the true spirit and scope of the novel concept of the present invention. It is to be understood that no limitation with respect to the specific embodiments illustrated herein is intended or should be inferred. The disclosure is intended to cover, by the appended claims, all such modifications as fall within the scope of the claims.

TABLE 1

| Example | Film Composition | MD Cantilever Bend (cm) | CD Cantilever Bend (cm) | Combined Cantilever Bend/Basis Weight | MD Flexural Rigidity (gm-cm) | CD Flexural Rigidity (gm-cm) | Combined Flexural Rigidity | WVTR (gm/m2/24 hours) |
|---|---|---|---|---|---|---|---|---|
| 1 | 80% LDPE 20% EMA | 3.2 | 3.1 | 0.19 | 0.081 | 0.069 | 0.15 | 48 |
| 2 | 100% EMA | 2.9 | 2.6 | 0.16 | 0.063 | 0.033 | 0.096 | 216 |
|   | Example 1 versus 2 |   |   | −16% |   |   | −36% | 350% |
| 3 | 20% LDPE 80% EMA | 3.2 | 2.5 | 0.17 | 0.080 | 0.036 | 0.12 | 141 |
|   | Example 1 versus 3 |   |   | −11% |   |   | −22% | 194% |
| 4 | 84% EMA 14% TiO2 2% CaCO3 | 2.8 | 2.5 | 0.16 | 0.041 | 0.039 | 0.08 | 181 |
|   | Example 1 versus 4 |   |   | −16% |   |   | −47% | 277% |
|   | Basis Weight for all samples = 34 gsm |   |   |   |   |   |   |   |

TABLE 2

|  | Basis Weight (gsm) | Strip Tensile (MD-g/cm) | Strip Tensile (CD-g/cm) | WVTR (gm/m$^2$/24 hrs) | Opacity (%) |
|---|---|---|---|---|---|
| Example 5 | 26.0 | 728.0 | 393.0 | 271 | 54.6 |
| Example 6 | 25.0 | 913.7 | 495.0 | 241 | 62.4 |

What is claimed is:
1. A film, comprising;
a blend a vinyl copolymer and at least one melt additive, said blend having at least 80% by weight of said vinyl copolymer, said blend formed into a monolithic film, and said monolithic film exhibiting an WVTR of at least about 140 and no more than about 450.

2. A breathable barrier film as in claim 1, wherein the melt additive is selected from the group consisting of colorants, softening agents, UV stabilizers, anti-static agents, hydrophobic compounds, hydrophilic compounds, and the combinations thereof.

3. A laminate material, comprising;

a first layer comprising a monolithic breathable barrier film, a second layer selected from the group consisting of apertured films, woven fabrics, nonwoven fabrics, and the combinations thereof, said breathable barrier film being formed from a blend of thermoplastic polymer and a vinyl copolymer, and extrusion-coated on said second layer, said blend having at least 80% by weight of said vinyl copolymer, said laminate material exhibiting an WVFR of at least about 140 and no more than about 450.

4. A breathable barrier laminate material as in claim 3, wherein said blend further comprises at least one melt additive.

5. A breathable barrier laminate material as in claim 3, wherein said laminate is used in the construction of a protective garment.

6. A disposable waste-containment garment, comprising;

an absorbent core, a liquid pervious topsheet, a liquid impervious backsheet, said liquid impervious backsheet comprising a monolithic breathable barrier film, said breathable barrier film formed of a vinyl copolymer, said breathable barrier film comprising at least 80% by weight of said vinyl copolymer, said laminate material exhibiting an WVTR of at least about 140 and no more than about 450, and said backsheet exhibiting an improvement of at least 10% reduction in drape, at least 22% reduction in flexural rigidity over a laminate containing less than or equal to 20% by weight of said vinyl copolymer.

7. A disposable waste-containment garment as in claim 5, wherein the garment is a diaper.

8. A disposable waste-containment garment as in claim 5, wherein the garment is a catamenial device.

* * * * *